US00RE46378E

(19) United States
(12) Reissued Patent
Evans et al.

(10) Patent Number: US RE46,378 E
(45) Date of Reissued Patent: Apr. 25, 2017

(54) ASSEMBLY FOR INSERTION OF AN OBJECT INTO A PIPELINE

(71) Applicant: Sentry Equipment Corp., Oconomowoc, WI (US)

(72) Inventors: Wilie V. Evans, Kilgore, TX (US); Gary K. Evans, Kilgore, TX (US)

(73) Assignee: SENTRY EQUIPMENT CORP., Oconomowoc, WI (US)

(21) Appl. No.: 14/608,060

(22) Filed: Jan. 28, 2015

Related U.S. Patent Documents

Reissue of:
(64) Patent No.: 8,359,937
Issued: Jan. 29, 2013
Appl. No.: 12/837,240
Filed: Jul. 15, 2010

(51) Int. Cl.
*G01N 33/00* (2006.01)
*G01N 17/04* (2006.01)

(52) U.S. Cl.
CPC ..... *G01N 17/046* (2013.01)

(58) Field of Classification Search
CPC ..... G01N 33/00
USPC ..... 422/53; 29/256; 73/86, 865.8; 285/284.1
See application file for complete search history.

(56) References Cited

U.S. PATENT DOCUMENTS 4,537,071 A * 8/1985 Waterman ..... B25B 27/143 73/866.5
4,633,713 A * 1/1987 Mesnard et al. ..... G01F 15/18 73/198
4,697,465 A * 10/1987 Evans ..... G01N 17/00 422/53
4,841,787 A * 6/1989 Waterman ..... G01F 1/40 374/E1.02
5,106,580 A * 4/1992 Mudiam ..... G01N 17/00 422/53
5,138,755 A * 8/1992 Evans ..... B25B 27/0028 29/256
5,953,801 A * 9/1999 Hulsebus ..... B25B 27/20 29/229

(Continued)

*Primary Examiner* — Joseph Kaufman
(74) *Attorney, Agent, or Firm* — Jansson Munger McKinley & Kirby Ltd.

(57) ABSTRACT

An assembly for insertion of an object into a pipeline comprises a base, a connector, and a set of pins. The base has a cylindrical passage and is connected to a mechanism [for] configured to drive the object into an inlet in the pipeline. The connector includes a head and a cylinder with a threaded internal surface and [a] *an* external surface having a groove [spanning a] *extending around the* circumference of the external surface. The connector is rotatable within the cylindrical passage in the base [in a first direction] and *is* held substantially *axially* stationary within the cylindrical passage in the base [in a second direction] by the set of pins in cooperation with the groove. [The base is rotatable in the first direction and held substantially stationary in the second direction while connected to the inlet in the pipeline by the connector.]

12 Claims, 5 Drawing Sheets

(56) References Cited

U.S. PATENT DOCUMENTS

| | | | | |
|---|---|---|---|---|
| 6,357,470 | B1 * | 3/2002 | Evans | F16L 41/16 137/315.01 |
| 7,886,624 | B1 * | 2/2011 | Mayeaux | G01N 1/2035 73/866.5 |
| 8,739,376 | B1 * | 6/2014 | Vidmar | B23P 19/00 29/239 |
| 2001/0020323 | A1 * | 9/2001 | Klann | B25B 27/0035 29/256 |

* cited by examiner

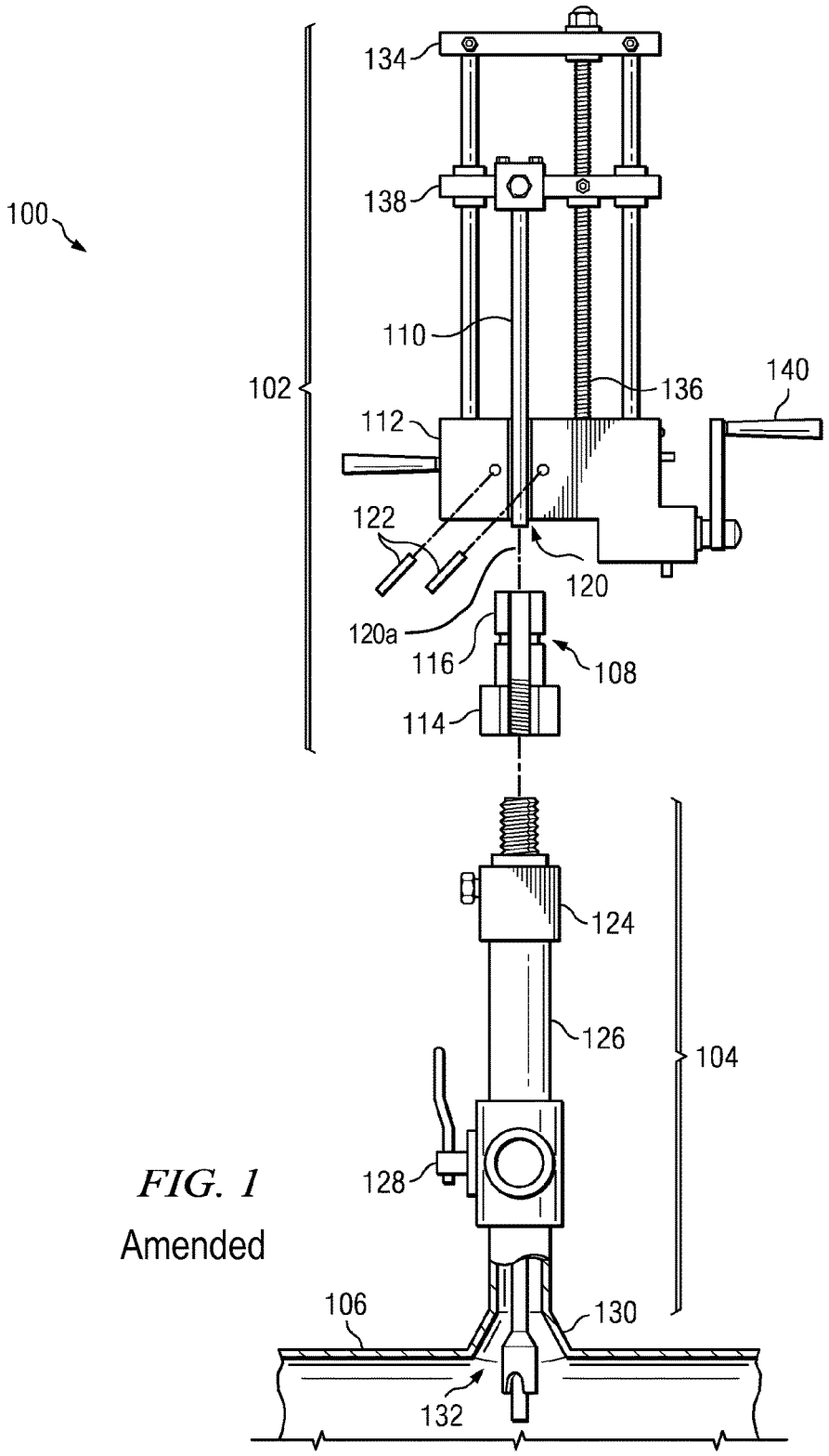
*FIG. 1*
Amended

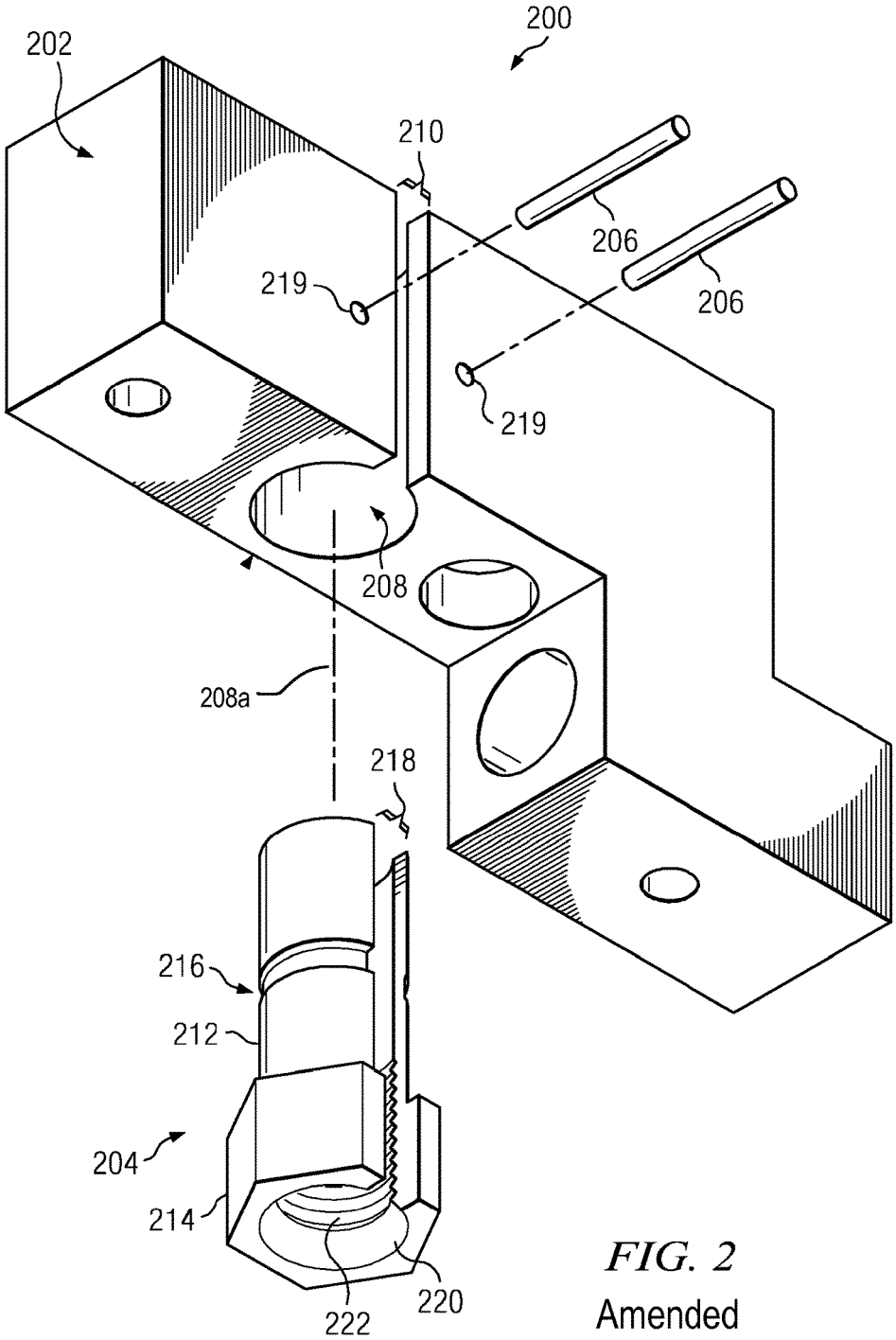
*FIG. 2*
Amended

ASSEMBLY FOR INSERTION OF AN OBJECT INTO A PIPELINE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

1. Field of the Invention

The present invention relates generally to insertion tools, and more specifically to an assembly for inserting test coupons into pressurized pipes or vessels.

2. Description of the Related Art

Tools and other devices are often required to be inserted into pressurized environments such as pipelines. For example, it is known that flow of potentially corrosive fluids or gases through a pipeline may cause corrosion and wear of the pipeline. Test coupons provide an inexpensive means of monitoring and measuring the corrosivity within a pipeline system. A corrosion coupon is inserted into a pressurized pipeline. Then, after some amount of time, the corrosion coupon is withdrawn from the pipeline. An operator of the pipeline may then be able to check for corrosion and wear of the pipeline based on the condition of the corrosion coupon withdrawn. By observing the corrosion rate of a coupon inserted and withdrawn from a pipeline, the pipeline's life expectancy may be predicted.

However, devices for inserting and withdrawing coupons into a pipeline often use threaded connections between various components of the device. The weight and size of components used in the device may cause difficulty in aligning the threads of connectors and connecting the components. Moreover, with repetitive use, connectors may become damaged or degraded. Damaged or degraded connectors may cause the entire device to become compromised leading to costly repairs. Additionally, the connections in the device need to be tightened sufficiently due to the pressure from the pipeline. Tightening a connection may result in components of the device being in a position where the components are not easily accessible by an operator of the device.

Accordingly, it would be advantageous to have a method and apparatus, which takes into account one or more of the issues discussed above as well as possibly other issues.

SUMMARY OF THE INVENTION

An embodiment of the present invention provides an apparatus for insertion of an object into a pipeline. The apparatus comprises a base, a connector, and a set of pins. The base has a cylindrical passage and is connected to a mechanism [for] configured to drive the object into an inlet in the pipeline. The connector includes a head and a cylinder with a threaded internal surface and a external surface having a groove [spanning] *extending around* a circumference of the external surface. The connector is rotatable within the cylindrical passage in the base [in a first direction] and *is* held substantially *axially* stationary within the cylindrical passage in the base [in a second direction] by the set of pins in cooperation with the groove. The base is rotatable [in the first direction] and held substantially *axially* stationary [in the second direction] while connected *with respect* to [the inlet in] the pipeline [by the connector].

Another embodiment of the present invention provides a method for connecting an apparatus for insertion of an object into a pipeline with an inlet in the pipeline. The method comprises inserting a outer surface of a connector into a cylindrical passage in a base. The outer surface of the connector has a groove [spanning] *extending around* a circumference of the connector. The connector is rotatable within the cylindrical passage in the base [in a first direction]. The base is connected to a mechanism [for] configured to drive the object into the inlet in the pipeline. The method further comprises rotating a head of the connector to connect a threaded inner surface of the connector to a threaded outer surface of [the inlet in] *a joint of a guide-assembly attached to* the pipeline and inserting a set of pins into the base and in cooperation with the groove to hold the connector substantially *axially* stationary within the cylindrical passage in the base [in a second direction]. The base is rotatable [in the first direction] and *is* held substantially *axially* stationary [in the second direction] while connected *with respect* to [the inlet in] the pipeline [by the connector].

Yet another embodiment of the present invention provides an apparatus for insertion of an object into a pipeline. The apparatus comprises a base, a connector, a set of pins, and a rod. The base has a cylindrical passage and is connected to a mechanism [for] configured to drive the object into an inlet in the pipeline. The connector includes a head and a cylinder with a threaded internal surface and a external surface having a groove [spanning] *extending around* a circumference of the external surface. The connector is rotatable within the cylindrical passage in the base [in a first direction] and *is* held substantially *axially* stationary within the cylindrical passage in the base [in a second direction] by the set of pins in cooperation with the groove. The threaded internal surface of the connector is [matched to be mated] *configured to mate* with an external threaded surface of the inlet in the pipeline. The rod is insertable into the connector through a slot formed in the base matched to a slot formed in the connector. The rod is passable through the cylindrical passage in the base, through the cylinder of the connector, and into the inlet in the pipeline. The rod is drivable into the inlet in the pipeline by the mechanism. The base is rotatable [in the first direction] and *is* held substantially *axially* stationary [in the second direction] while connected *with respect* to [the inlet in] the pipeline [by the connector].

BRIEF DESCRIPTION OF THE DRAWINGS

The foregoing and other features and aspects of the present invention will be best appreciated by reference to a detailed description of some specific embodiments of the invention, when read in conjunction with the accompanying drawings, wherein:

FIG. 1 is an exploded view of an assembly of an apparatus for coupon insertion withdrawal in accordance with an illustrative embodiment;

FIG. 2 is an exploded view of a connection section in an apparatus for coupon insertion withdrawal in accordance with an illustrative embodiment;

DETAILED DESCRIPTION

Figure 3:
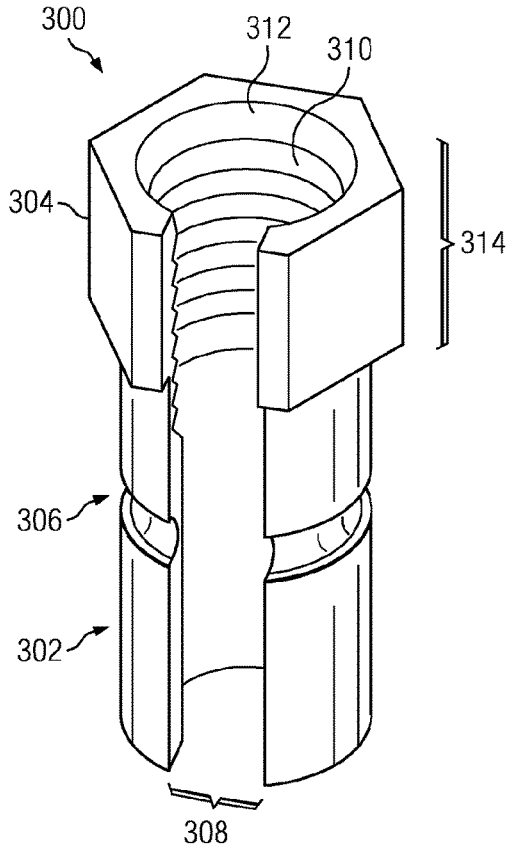
FIG. 3 is a perspective view of a connector in accordance with an illustrative embodiment.

In the disclosure that follows, in the interest of clarity, not all features of actual implementations are described. It will of course be appreciated that in the development of any such actual implementation, as in any such project, numerous engineering and technical decisions must be made to achieve the developers' specific goals and subgoals which will vary from one implementation to another. For example, the developers' specific goals and subgoals may include compliance with system and technical constraints. Moreover, attention will necessarily be paid to proper engineering practices for the environment in question. It will be appreciated that such a development effort might be complex and time-consuming, but would nevertheless be a routine undertaking for those of ordinary skill in the relevant fields.

The different advantageous embodiments recognize and take into account a number of different considerations. For example, the different advantageous embodiments recognize that it may be desirable to have components in an apparatus for coupon insertion and withdrawal that are easy to connect. The different advantageous embodiments recognize that one solution may involve using threaded connectors to connect the components. However, the different advantageous embodiments recognize that components in an apparatus for coupon insertion and withdrawal may be heavy and cumbersome and that threaded connectors may be difficult to align. The different advantageous embodiments also take into account that using threaded connectors may result in components of the apparatus being positioned in inconvenient positions. Further, the different advantageous embodiments recognize that it may be desirable to have connectors in an apparatus for coupon insertion and withdrawal that may be replaced without the need to replace other components in the apparatus.

Thus, the different advantageous embodiments provide an apparatus for insertion of an object into a pipeline. The apparatus comprises a base, a connector, and a set of pins. The base has a cylindrical passage and is connected to a mechanism [for] configured to drive the object into an inlet in the pipeline. The connector includes a head and a cylinder with a threaded internal surface and [a] *an* external surface having a groove [spanning] *extending around* a circumference of the external surface. The connector is rotatable within the cylindrical passage in the base [in a first direction] and *is* held substantially *axially* stationary within the cylindrical passage in the base [in a second direction] by the set of pins in cooperation with the groove. The base is rotatable [in the first direction] and *is* held substantially *axially* stationary [in the second direction] while connected *with respect* to [the inlet in] the pipeline [by the connector].

As used herein, a first component may be connected with a second component by being secured to the second component, bonded to the second component, fastened to the second component, and/or mounted to the second component in some other suitable manner. The first component also may be connected to the second component through using a third component. The first component may also be considered to be connected with the second component by being formed as part of and/or an extension of the second component. Also, as used herein "a set", when referring to items, means one or more items.

With reference now to the figures and particularly with reference now to FIG. 1, an illustration of an exploded view of an assembly of an apparatus for coupon insertion and withdrawal is depicted in accordance with an embodiment of the invention. As illustrated, assembly 100 includes driving mechanism 102 and guide assembly 104 connected to pipeline 106. Guide assembly 104 is mounted on pipeline 106. Driving mechanism 102 is connected *to* guide assembly 104 using connector 108. Driving mechanism 102 may then be used to drive rod 110 through guide assembly 104 into pipeline 106.

In this illustrative embodiment, connector 108 can connect base 112 of driving mechanism 102 with guide assembly 104. For example, connector 108 includes cylinder [114] *116* and head [116] *114*. Base 112 includes cylindrical passage 120 within base 112 of driving mechanism 102*; cylindrical passage 120 defines an axis 120a*. Cylinder [114] *116* of connector 108 may be inserted into cylindrical passage 120 within base 112. Cylinder [114] *116* of connector 108 may also rotate within cylindrical passage 120 of base 112. Set of pins 122 can be inserted into base 112 to maintain [a] *an axial* position of cylinder [114] *116* within cylindrical passage 120 of base 112. Head [116] *114* of connector 108 can be connected to guide assembly 104. Thus, driving mechanism 102 is connected to guide assembly 104 using connector 108. Further, due to the insertion of cylinder [114] *116* into cylindrical passage 120 of base 112, driving mechanism 102 can be rotated [in a direction] while being connected to guide assembly 104.

As depicted, guide assembly 104 includes joint 124 connected to guide body 126 and valve 128. Guide assembly 104 is connected to saddle 130 on pipeline 106. The combination of guide assembly 104 with saddle 130 creates inlet 132 in pipeline 106. Inlet 132 provides an opening for insertion of rod 110 into pipeline 106. Valve 128 provides a means to open or seal inlet 132 in pipeline 106.

In this illustrative embodiment, joint 124 may be a packer joint for receiving rod 110 through a cylindrical passage in joint 124. Due to the fact that pipeline 106 may have a pressure inside of pipeline 106 that is greater than the pressure outside of pipeline 106, joint 124 may include a seal to maintain the pressure within pipeline 106. For example, the cylindrical passage in joint 124 may have a diameter that is substantially the same as a diameter of rod 110. Thus, as driving mechanism 102 drives rod 110 into inlet 132 in pipeline 106, the combination of the diameter of rod 110 matched with the diameter of the cylindrical passage in joint 124 acts as a seal to maintain the pressure within pipeline 106. Joint 124 may also be a holder for an object to be inserted into pipeline 106. For example, joint 124 may be a coupon holder that includes a corrosion coupon in the cylindrical passage within joint 124. The corrosion coupon may be used by an operator of pipeline 106 to determine an amount of corrositivity within pipeline 106. As rod 110 is driven through joint 124, the coupon included in joint 124 is forced from joint 124 through inlet 132 and into pipeline 106.

In this illustrative embodiment, driving mechanism 102 may employ a number of different methods to drive or withdraw rod 110 into or from inlet 132 in pipeline 106. In this example, driving mechanism 102 includes frame 134, threaded rod 136, cross bar 138, and crank 140 connected to base 112. Threaded rod 136 is rotatably mounted between frame 134 and base 112. Cross bar 138 is in threaded engagement with threaded rod 136. In driving mechanism 102, base 112 acts as an assembly adapted to transmit power from crank 140 to rod 110. For example, rotation of crank 140 through base 112 rotates threaded rod 136 and moves cross bar 138. Thus, as crank 140 is rotated, a portion of rod 110 is caused to move in or out through guide assembly 104.

The illustration of an assembly of an apparatus for coupon insertion and withdrawal in FIG. 1 is not meant to imply physical or architectural limitations to the manner in which different advantageous embodiments may be implemented. Other components in addition and/or in place of the ones illustrated may be used. Some components may be unnecessary in some advantageous embodiments. In some examples, a pair of dowels or a ring may be used in place of set of pins 122 to maintain the *axial* position of cylinder [114] *116* within cylindrical passage 120 of base 112. In other examples, one or more pins may be used in place of set of pins 122; set of pins 122 may also be inserted lengthwise into base 112. Yet in other examples, multiple threaded rods may be used instead of one threaded rod.

With reference now to FIG. 2, an illustration of an exploded view of a connection section in an apparatus for coupon insertion *and* withdrawal is depicted in accordance with an embodiment. Connection section 200 is a detailed view of a connection between a driving mechanism, such as driving mechanism 102 in FIG. 1, and a guide assembly, such as guide assembly 104 in FIG. 1. As depicted, connection section 200 includes base 202, connector 204, and set of pins 206. Base 202, connector 204, and set of pins 206 may be examples of implementations of base 112, connector 108, and set of pins 122 in FIG. 1.

In this illustrative embodiment, base 202 includes cylindrical passage 208 through base 202 and slot 210 formed in base 202. Cylindrical passage 208, *which defines axis 208a,* is adapted for insertion of connector 204 into base 202. Connector 204 includes cylinder 212, head 214, groove 216 and slot 218 formed in connector 204. Groove 216 is formed in cylinder 212 of connector 204. In this example, groove 216 extends [across] *around* a circumference of cylinder 212 on an exterior surface of cylinder 212.

When cylinder 212 of connector 204 is inserted into cylindrical passage 208 of base 202, set of pins 206 may be inserted into holes 219 in base 202 to maintain [a] *an axial* position of cylinder 212 within base 202. For example, set of pins 206 inserted into base 202 may work in cooperation with groove 216 in cylinder 212 to maintain the *axial* position of cylinder 212 within base 202. Set of pins 206 may contact groove 216 and pass through groove 216 on opposite sides of cylinder 212.

The cooperation of groove 216 with set of pins 206 causes a vertical position of the connector to be maintained with respect to base 202. Additionally, the cooperation of groove 216 with set of pins 206 permits cylinder 212 of connector 204 to rotate within cylindrical passage 208 in base 202. Thus, cooperation of groove 216 with set of pins 206 enables connector 202 to remain connected to base 202 while allowing rotation of connector 204 with respect to base 202.

Rotation of connector 204 with respect to base 202 permits alignment of slot 210 in base 202 with slot 218 in connector 204. Alignment of slot 210 in base 202 with slot 218 in connector 204 may be desirable when inserting or removing a rod used to drive an object into a pipeline. For example, a rod, such as rod 110 in FIG. 1, may be inserted through and/or removed from cylindrical passage 208 in base 202 and connector 204. In addition, a rod, such as rod 110 in FIG. 1, may be inserted in or removed from base 202 and connector 204 using slot 210 in base 202 aligned with slot 218 in connector 204. The use of slot 210 in base 202 and slot 218 in connector 204 may be advantageous in situations where space is limited and/or replacement of connector 204 is desired. For example, if connector 204 needed to be removed, an operator would simply just have to slide the base and/or connector from around the rod using slot 218 in connector 204 and/or slot 210 in base 202. Connector 204 may be removed without the need to either completely withdraw the rod from the inlet in the pipeline or raise base 202 and connector 208 above a length of the rod. Additionally, the size of slot 218 in connector 204 may be selected based upon a diameter of the rod.

In this illustrative example, connector 204 includes inner surface 220 having threads 222 inside head 214. Threads 222 on inner surface 220 of connector 204 may be matched to threads on a joint, such as for example joint 124 in FIG. 1, to connect connector 204 to an inlet in a pipeline such as for example pipeline 106 in FIG. 1. Threads 222 may be rotated to tighten connector 204 to an inlet in the pipeline using head 214. In this example, head 214 has a hexagonal shape. The hexagonal shape of head 214 may be selected to allow an operator to tighten connector 204 with an inlet in a pipeline using tools such as a wrench, for example. Additionally, threads 222 may extend a length into inner surface 220 of connector 204. The distance threads 222 extend in inner surface 220 may be selected to allow an increased amount of tightening of connector 204 with an inlet into a pipeline. For example, an inlet of a pipeline may include a threaded surface matched to be mated with threads 222 on connector 204. Threads 222 may be selected to extend a length into connector 204 that is greater than a length of the threaded surface on the inlet into the pipeline. This selection of threads 222 allow for connector 204 to be tightened beyond the length of the threaded surface on the inlet into the pipeline without bottoming out on threads 222 in connector 204.

In these examples, the materials used to make base 202 and connector 204 may be selected to reduce an amount of galling between base 202 and connector 204. Galling generally refers to adhesive wear and transfer of material between metallic surfaces. For example, rotation of connector 204 in base 202 may result in wear or transfer of materials between base 202 and connector 204. Thus, base 202 and connector 204 may be made of materials selected to reduce an amount of galling between base 202 and connector 204. In one example, connector 204 may be made from brass, while base 202 may be made from aluminum. In other examples, connector 204 and base 202 may be made from any material or combination of materials known to reduce an amount of galling between mechanical surfaces.

With reference now to FIG. 3, an illustration of a perspective view of a connector is depicted in accordance with an illustrative embodiment. Connector 300 may be an example of one implementation of connector 108 in FIG. 1. As depicted, connector 300 includes cylinder 302, head 304, groove 306, and slot 308 formed in connector 300. Groove 306 is formed in cylinder 302 of connector 300 and extends around the circumference of cylinder 302. Connector 300 further includes threads 310 formed in inner surface 312 of connector 300. As depicted threads 310 extend length 314 into inner surface 312 of connector 300.

Figure 4:
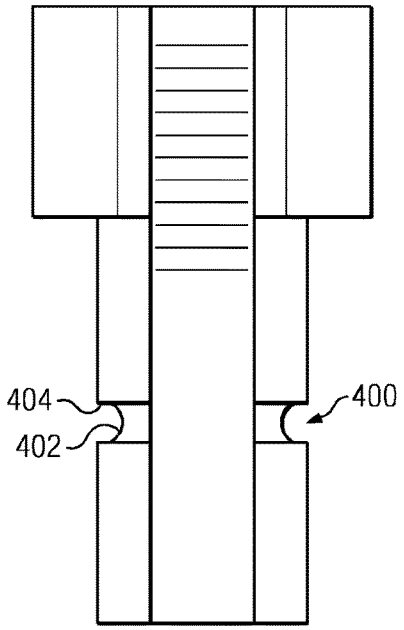
FIG. 4 is a side view of the connector in FIG. 3 in accordance with an illustrative embodiment.

With reference now to FIG. 4, an illustration of a cross-sectional view of connector 300 in FIG. 3 is depicted in accordance with an illustrative embodiment. In this illustrative embodiment, groove 400 may be an example of one embodiment of groove 216 in FIG. 2. As depicted, groove 400 includes rounded inner surface 402 and flat surfaces 404. In this example the shape of groove 400 to include rounded inner surface 402 and flat surfaces 404 may be selected based on a set of pins, such as set of pins 206 in FIG. 2, that work in cooperation with groove 400.

Figure 5:
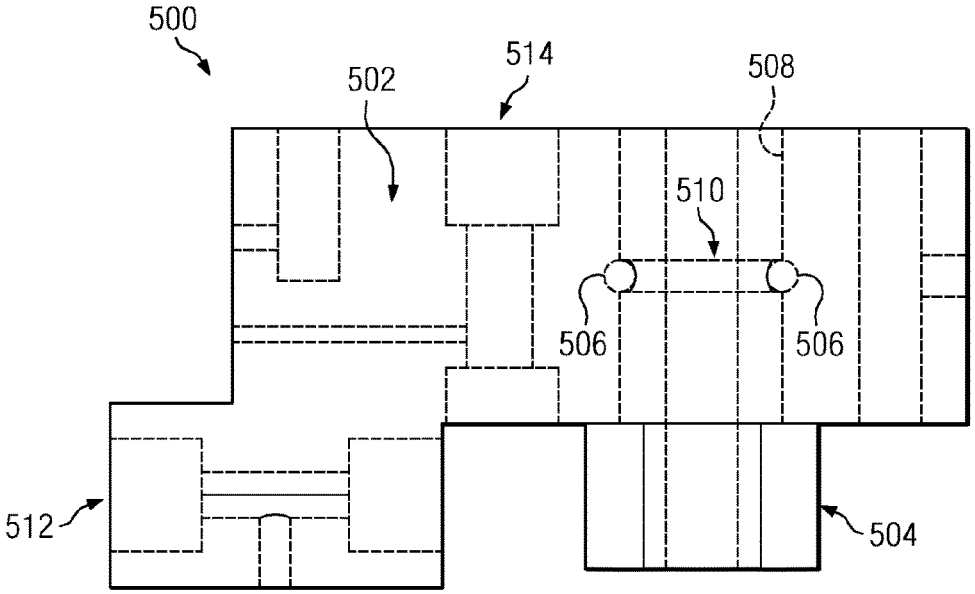
FIG. 5 is a cross-sectional view of an assembled connection section in accordance with an illustrative embodiment.

With reference now to FIG. 5, a cross-sectional view of an assembled connection section is depicted in accordance with an illustrative embodiment. In this illustrative embodiment, connection section 500 may be an example of one implementation of connection section 200 in FIG. 2. As depicted, connection section 500 includes base 502, connector 504, and set of pins 506. Connector 504 includes cylinder 508 inserted into base 502. Connector 504 further includes groove 510 formed in cylinder 508. Set of pins 506 are inserted into base 502. Set of pins 506 work in cooperation with groove 510 to hold cylinder 508 within base 502, while permitting rotation of cylinder 508 within base 502. Additionally, base 502 may include cavities 512 and 514 for the insertion of other components such as, for example, a crank, such as crank 140 in FIG. 1, or a threaded rod, such as threaded rod 136 in FIG. 1, into base 502.

Figure 6:
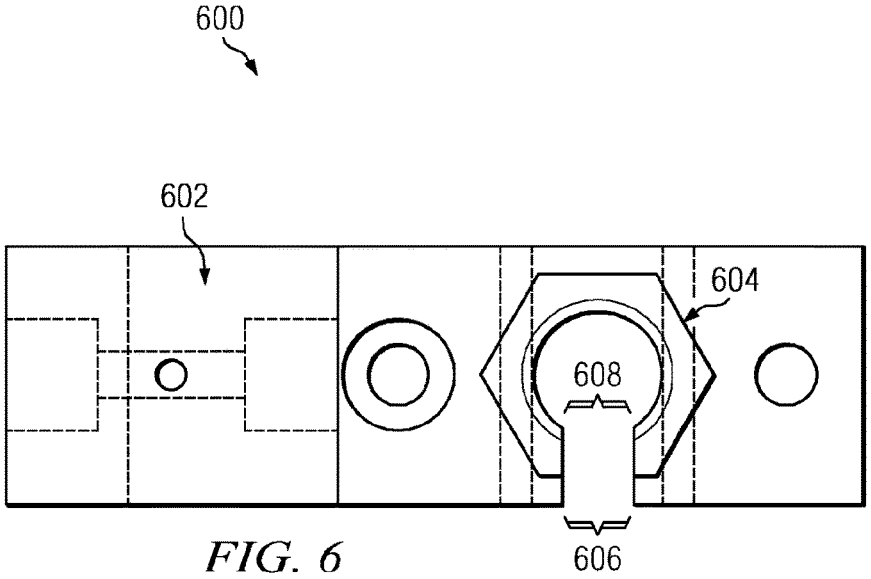
FIG. 6 is an alternate view of the assembled connection section in FIG. 5 in accordance with an illustrative embodiment.

With reference now to FIG. 6, an alternate view of the assembled connection section in FIG. 5 is depicted in accordance with an illustrative embodiment. In this illustration, connection section 600 provides an alternate view, such as for example a bottom view, of connection section 500 in FIG. 5. As depicted, connection section 600 includes base 602 and connector 604. In this example, slot 606 formed in base 602 is aligned with slot 608 in connector 604.

Figure 7:
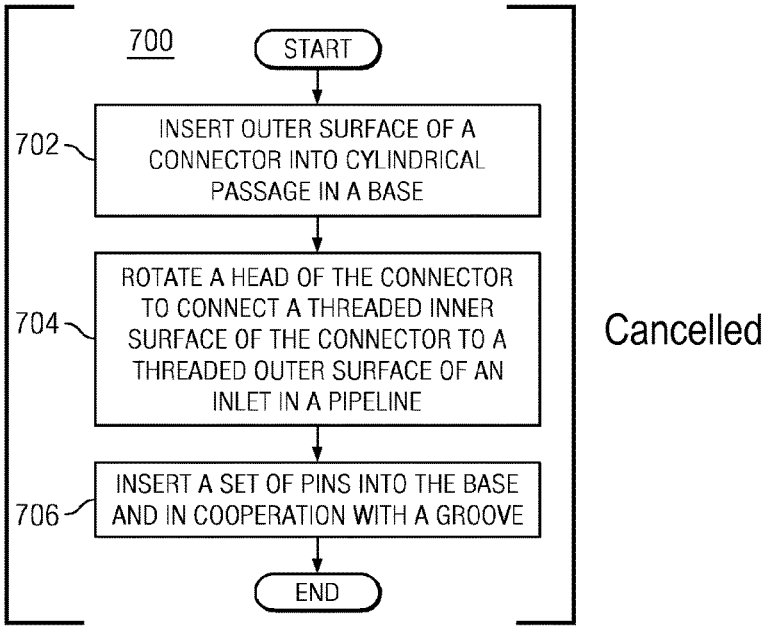
FIG. 7 is a flowchart illustrating a process for connecting an apparatus for insertion of an object into a pipeline with an inlet in the pipeline in accordance with an illustrative embodiment.

[With reference now to FIG. 7, a flowchart illustrating a process for connecting an apparatus for insertion of an object into a pipeline with an inlet in the pipeline is depicted in accordance with an illustrative embodiment. Process 700 begins by inserting an outer surface of a connector into a cylindrical passage in a base (operation 702). The connector may be a connector such as connector 108 in FIG. 1. In operation 702, the outer surface of the connector may have a groove spanning a circumference of the connector. The connector is rotatable within the cylindrical passage in the base in a first direction. The base is connected to a mechanism, such as driving mechanism 102 in FIG. 2, for driving the object into the inlet in the pipeline. Process 700 then rotates a head of the connector to connect a threaded inner surface of the connector to a threaded outer surface of the inlet in the pipeline (operation 704). In operation 704, the base is rotatable in the first direction and held substantially stationary in the second direction while connected to the inlet in the pipeline by the connector. Thereafter, process 700 inserts a set of pins into the base and in cooperation with the groove (operation 706), with process 700 terminating thereafter. In operation 706, the set of pins in cooperation with the groove may operate to hold the connector substantially stationary within the cylindrical passage in the base in a second direction.]

Figure 8:
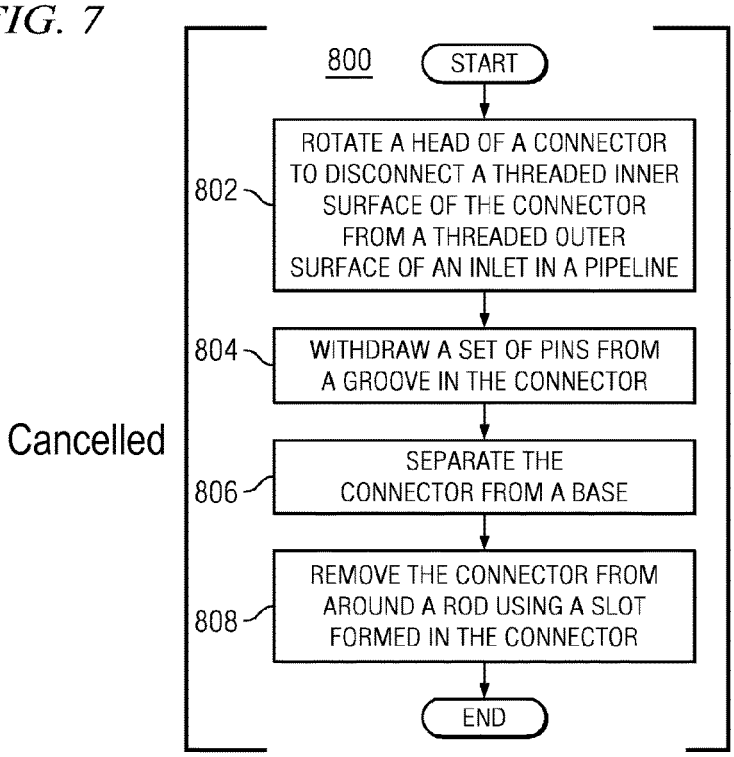
FIG. 8 is a flowchart illustrating a process for removing a connector from an apparatus for insertion of an object into a pipeline in accordance with an illustrative embodiment.

[With reference now to FIG. 8, a flowchart illustrating a process for removing a connector from an apparatus for insertion of an object into a pipeline is depicted in accordance with an illustrative embodiment. Process 800 illustrated in FIG. 8 may be implemented using an apparatus connected according to process 700 illustrated in FIG. 7. Process 800 begins by rotating a head of the connector to disconnect a threaded inner surface of the connector from a threaded outer surface of an inlet in the pipeline (operation 802). In operation, 802 the connector may have a slot formed in the connector that extends an entire length of the connector. Process 800 then withdraws a set of pins from a groove in the connector (operation 804). In operation 804, the set of pins in cooperation with the groove may operate to maintain a position of the connector within a base. Process 800 separates the connector from the base (operation 806). In operation 806, the base may be moved from the inlet in the pipeline to allow for the connector to separate from the base. Thereafter, process 800 removes the connector from around a rod using the slot formed in the connector (operation 808), with process 800 terminating thereafter. In operation 808, the rod may be inserted into the inlet in the pipeline. Using the slot formed in the connector, the connector may be removed from the apparatus while the rod remains inserted in the base and inlet.]

[The flowcharts and block diagrams in the different depicted embodiments illustrate the architecture, functionality, and operation of some possible implementations of apparatus and methods in different advantageous embodiments. In this regard, each block in the flowchart or block diagrams may represent a module, segment, function, and/or a portion of an operation or step. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved. Also, other blocks may be added in addition to the illustrated blocks in a flowchart or block diagram.]

Thus, the different illustrative embodiments provide for an apparatus and method for insertion of an object into a pipeline. In one embodiment, the connector may be rotated within the base while remaining connected to the base. This may be particularly advantageous in situations where it is desirable to connect a driving mechanism to an inlet in the pipeline without rotating the entire driving mechanism. The cylinder of the connector and the cooperation of the set of pins with the groove in the connector allow the driving mechanism to be connected to an inlet in a pipeline without having to rotate the driving mechanism. In other embodiments, the driving mechanism may be rotated around the connector while remaining connected to the inlet in the pipeline. It may be desirable for a driving mechanism to be positioned in a particular manner after the driving mechanism is connected to an inlet in the pipeline. For example, in situations where space may be tight, it may be desirable to have a crank connected to the driving mechanism in a particular position so that an operator may rotate the crank. The cylinder of the connector and the cooperation of the set of pins with the groove in the connector allow the driving mechanism to rotate about the connector while the driving mechanism is connected to the inlet in the pipeline.

Additionally, the slot formed in the connector and the slot formed in the base for the driving mechanism may be particularly advantageous for inserting a rod into the inlet in the pipeline once the driving mechanism is connected to the inlet. The rod may be inserted into the driving mechanism using the slot formed in the connector and the slot formed in the base rather than requiring that the rod be fed through the driving mechanism. Further, the slot formed in the connector is particularly advantageous in removing the base and/or connector from the inlet in the pipeline once the rod is inserted into the pipeline. The base and/or connector may be removed from around the rod using the slot without removing the rod from the inlet in the pipeline and without the need to raise the base and/or connector above a height of the rod.

The description of the different illustrative embodiments has been presented for purposes of illustration and description, and is not intended to be exhaustive or limited to the embodiments in the form disclosed. Many modifications and variations will be apparent to those of ordinary skill in the art. Further, different embodiments may provide different advantages as compared to other embodiments. The embodiment or embodiments selected are chosen and described in order to best explain the principles of the invention, the practical application, and to enable others of ordinary skill in the art to understand the invention for various embodiments with various modifications as are suited to the particular use contemplated.

What is claimed is:

1. An apparatus for insertion of an object into a pipeline, the apparatus comprising:

a base having a cylindrical passage *defining an axis*, the base connected to a mechanism configured to drive the object into an inlet in the pipeline;

a connector including a head and a cylinder with a threaded internal surface and [a] *an* external surface having a groove [spanning] *extending around* a circumference of the external surface, the connector rotatable within the cylindrical passage in the base [in a first direction] and held substantially *axially* stationary within the cylindrical passage in the base [in a second direction] by a set of pins in cooperation with the groove[; and wherein the base is rotatable in the first direction and held substantially stationary in the second direction while connected to the inlet in the pipeline by the connector].

2. The apparatus of claim 1 further comprising[:] a rod insertable into the connector through a slot formed in the base matched to a slot formed in the connector, the rod passable through the cylindrical passage in the base, through the cylinder of the connector, and into the inlet in the pipeline, the rod drivable into the inlet in the pipeline by the mechanism.

3. The apparatus of claim 2 *further including a guide assembly connected to the pipeline and having a joint for attachment with the connector*, the rod [having an] outer diameter [with a dimension] *being* substantially the same as [a dimension of an inner diameter of the inlet in the pipeline] *a cylindrical passage in the joint*.

4. The apparatus of claim 2[,] wherein rotation of the connector within the base aligns the slot formed in the base with the slot formed in the connector.

5. The apparatus of claim 2[,] wherein the slot formed in the connector extends [an] *the* entire length of the connector.

6. The apparatus of claim [1,] *3* wherein the threaded internal surface of the connector is [matched] *configured* to [be mated] *mate* with an external threaded surface of the [inlet in the pipeline] *joint*.

7. The apparatus of claim 1[,] wherein the object is a coupon *for* indicating a level of corrosion within the pipeline.

8. The apparatus of claim 1[,] wherein the head of the connector is hexagonal.

9. The apparatus of claim 1[,] wherein the base remains *axially* substantially stationary while the connector is rotated to connect to the inlet.

10. The apparatus of claim 1[,] wherein the connector is made from a material selected to reduce [an amount of] galling between the connector and the base.

11. The apparatus of claim 1[,] wherein the base is made [from a material comprising] *of* aluminum.

12. The apparatus of claim 1[,] wherein the connector is made [from a material comprising] *of* brass.

[13. An apparatus for insertion of an object into a pipeline, the apparatus comprising:

a base having a cylindrical passage, the base connected to a mechanism for configured to drive the object into an inlet in the pipeline;

a connector including a head and a cylinder with a threaded internal surface and a external surface having a groove spanning a circumference of the external surface, the connector rotatable within the cylindrical passage in the base in a first direction and held substantially stationary within the cylindrical passage in the base in a second direction by a set of pins in cooperation with the groove, the threaded internal surface of the connector matched to be mated with an external threaded surface of the inlet in the pipeline;

a rod insertable into the connector through a slot formed in the base matched to a slot formed in the connector, the rod passable through the cylindrical passage in the base, through the cylinder of the connector, and into the inlet in the pipeline, the rod drivable into the inlet in the pipeline by the mechanism; and wherein the base is rotatable in the first direction and held substantially stationary in the second direction while connected to the inlet in the pipeline by the connector.]

[14. The apparatus of claim 13, the rod having an outer diameter with a dimension substantially the same as a dimension of an inner diameter of the inlet in the pipeline.]

[15. The apparatus of claim 13, wherein rotation of the connector within the base aligns the slot formed in the base with the slot formed in the connector.]

[16. The apparatus of claim 13, wherein the slot formed in the connector extends an entire length of the connector.]

[17. A method for connecting an apparatus for insertion of an object into a pipeline with an inlet in the pipeline, the method comprising:

inserting a outer surface of a connector into a cylindrical passage in a base, wherein the outer surface of the connector has a groove spanning a circumference of the connector, wherein the connector is rotatable within the cylindrical passage in the base in a first direction, wherein the base is connected to a mechanism for configured to drive the object into the inlet in the pipeline;

rotating a head of the connector to connect a threaded inner surface of the connector to a threaded outer surface of the inlet in the pipeline; and inserting a set of pins into the base and in cooperation with the groove to hold the connector substantially stationary within the cylindrical passage in the base in a second direction, wherein the base is rotatable in the first direction and held substantially stationary in the second direction while connected to the inlet in the pipeline by the connector.]

[18. The method of claim 17 further comprising:

rotating the base about the connector to align a slot formed in the base with a slot formed in the connector; and inserting a rod into the connector through the slot formed in the base and the slot formed in the connector, wherein the rod is drivable into the inlet using the mechanism.]

[19. The apparatus of claim 18, wherein the slot formed in the connector extends an entire length of the connector further comprising:

removing the connector by rotating a head of the connector to disconnect the threaded inner surface of the connector from the threaded outer surface of the inlet in the pipeline, withdrawing the set of pins from the groove, separating the connector from the base, and removing the connector from around the rod using the slot formed in the connector while the rod remains inserted in the base and inlet.]

[20. The method of claim 17, wherein the connector is made from a material selected to reduce an amount of galling between the connector and the base.]

* * * * *